United States Patent [19]
Ishihara et al.

[11] Patent Number: 5,124,494
[45] Date of Patent: Jun. 23, 1992

[54] CONTINUOUS PROCESS FOR PREPARING CHLOROTRIFLUOROETHYLENE

[75] Inventors: Akira Ishihara, Tokorozawa; Takeshi Asanawa, Kamifukuoka; Satoshi Nakahata, Saitama; Takashi Yasumura, Fujimi, all of Japan

[73] Assignee: Central Glass Company, Limited, Ube, Japan

[21] Appl. No.: 732,834

[22] Filed: Jul. 19, 1991

[30] Foreign Application Priority Data

Jul. 20, 1990 [JP] Japan ................. 2-192420

[51] Int. Cl.⁵ .................................. C07C 17/34
[52] U.S. Cl. ................................... 570/158
[58] Field of Search ......................... 570/158

[56] References Cited

U.S. PATENT DOCUMENTS 2,831,901 4/1958 Rearick et al.
2,877,275 3/1959 Jewell.

FOREIGN PATENT DOCUMENTS 0115305 9/1979 Japan ................. 570/158

Primary Examiner—Alan Siegel
Attorney, Agent, or Firm—Fleit, Jacobson, Cohn, Price, Holman & Stern

[57] ABSTRACT

The subject is the preparation of chlorotrifluoroethylene (CTFE) by a known reaction of 1,1,2-trichloro-1,2,2-trifluoroethane (R-113) with zinc powder dispersed in an alcohol such as methanol, and the object of the invention is industrially easily and smoothly carrying out the reaction in a continuous manner. The disclosed process uses a plurality of stirred tank reactors, usually two or three reactors, which are connected to each other in a series arrangement by overflow pipes. A dispersion of zinc powder in an alcohol is continuously fed into the first reactor only so as to allow the dispersion to overflow into the next reactor and then into the remaining reactor(s) in turn, and R-113 is continuously fed into each reactor. CTFE is continuously discharged from each reactor, while zinc in the initially fed dispersion is gradually converted into zinc chloride. In the last reactor the conversion of zinc reaches 90% or above. Together with the remaining zinc powder the solution of zinc chloride in the alcohol is continuously discharged from the last reactor and can easily be recovered.

11 Claims, 1 Drawing Sheet

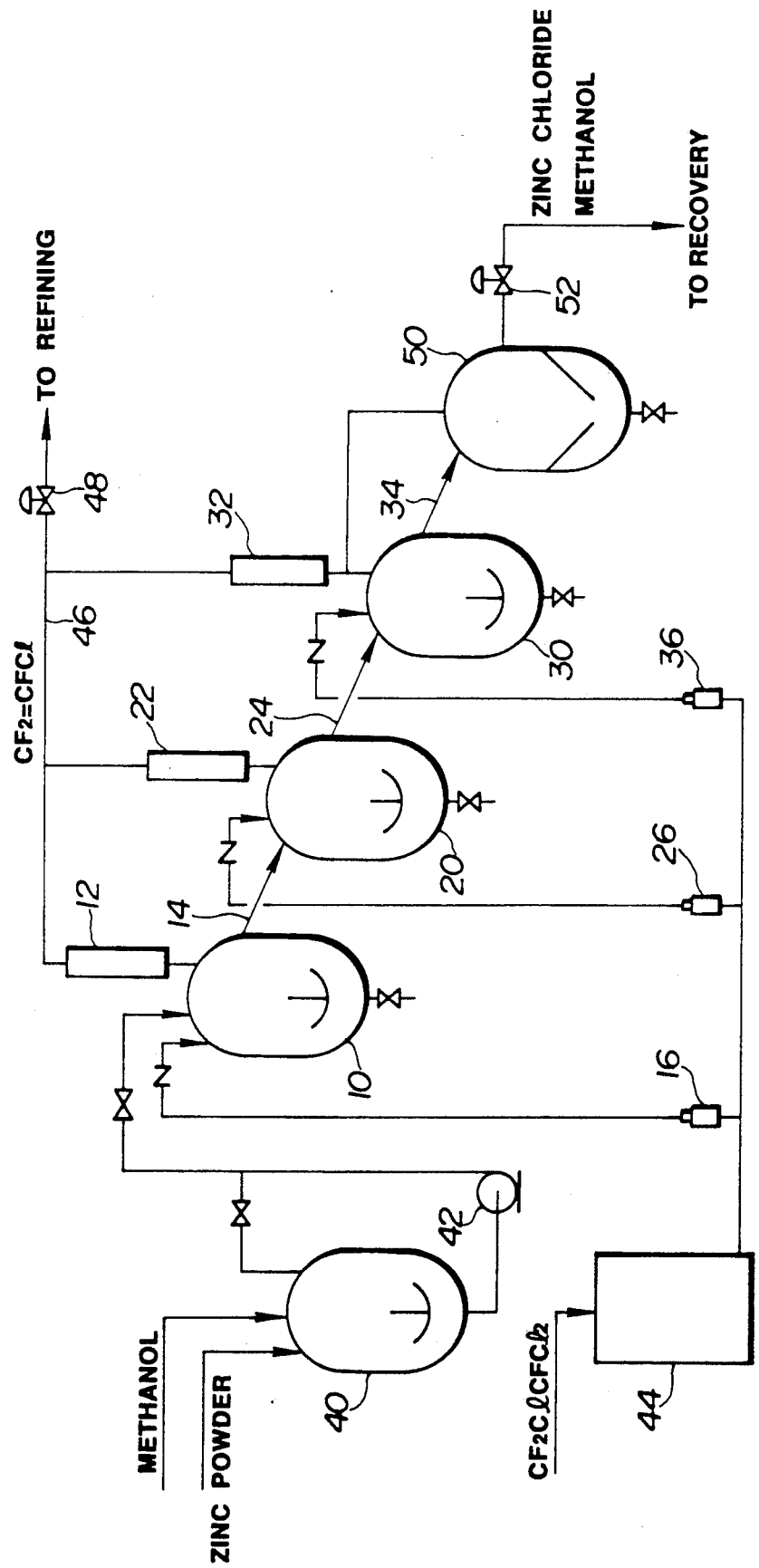

CONTINUOUS PROCESS FOR PREPARING CHLOROTRIFLUOROETHYLENE

BACKGROUND OF THE INVENTION

This invention relates to a continuous process for industrially preparing chlorotrifluoroethylene by the reaction of 1,1,2-trichloro-1,2,2-trifluoroethane with zinc powder in an alcohol.

In the field of fluororesins and fluorine rubbers, chlorotrifluoroethylene (CTFE) is an important monomer for both polychlorotrifluoroethylene and various copolymers with, for example, ethylene, vinyl acetate or vinylidene fluoride.

As an industrial material CTFE is usually prepared from 1,1,2-trichloro-1,2,2-trifluoroethane (herein called "R-113"), and a prevailing method is to add R-113 to a dispersion of zinc powder in a lower alcohol, as shown in U.S. Pat. No. 2,831,901 by way of example.

Also it is possible to prepare CTFE by reacting R-113 with hydrogen in the presence of a copper, nickel or cobalt catalyst on a suitable carrier. This reaction seems to be favorable for industrial practice because of the simplicity of the operation, but actually this reaction is low in the selectivity to CTFE and the yield of same, and the product contains large amounts of impurities or by-products so that it is difficult to obtain high-purity CTFE suitable for polymerization by usual refining operations including distillation. Therefore, this reaction has not been employed as an industrial process.

The reaction of R-113 with zinc powder, which is represented by the following equation, is advantageous in that the reaction proceeds nearly stoichiometrically and that CTFE of sufficiently high purity can be obtained.

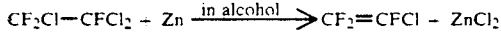

$$CF_2Cl-CFCl_2 + Zn \xrightarrow{\text{in alcohol}} CF_2=CFCl + ZnCl_2$$

In industrial practice this reaction is usually carried out by a batch process, and, as explained below, there are some problems which are almost inherent to a batch process.

(1) The reaction terminates as the entire quantity of initially charged zinc powder is consumed. Every time the reaction terminates, it is necessary to discharge zinc chloride formed by the reaction from the reactor together with the alcohol and newly charge the reactor with zinc powder and alcohol, followed by the replacement of the gas atmosphere in the reactor by an inactive gas such as nitrogen gas. These are troublesome operations and entail the loss of considerable time.

(2) The aforementioned inactive gas is liable to intrude into CTFE formed by the reaction.

(3) At the last stage of gradual consumption of zinc powder (after the conversion of about 80% of zinc in the reactor into zinc chloride) the rate of formation of CTFE becomes low so that a considerable change occurs in the flow rate of the reaction product, and accordingly there arises the need of varying some items of operation conditions.

There are proposals of carrying out the same reaction by a continuous process using a tray tower: e.g., U.S. Pat. No. 2,877,275, JP 47-45322 and JP 57-5207. However, when any of the hitherto proposed continuous processes is put into practice on an industrial scale there are some problems such as lowness of the conversion of zinc into zinc chloride and unstableness of operation by reason of difficulty of uniformly dispersing zinc powder in the continuously flowing alcohol and consequential accumulation of zinc powder in the tray tower or the piping, sometimes resulting in choking.

SUMMARY OF THE INVENTION

It is an object of the present invention to provide an improved continuous process for the preparation of CTFE by the reaction of R-113 with zinc powder, which process can easily be put into industrial practice with good stability of operations and can accomplish sufficiently high conversion of zinc fed into the reaction system.

The present invention provides a process of preparing CTFE by continuously reacting 1,1,2-trichloro-1,2,2-trifluoroethane with zinc powder dispersed in an alkyl alcohol, the process is characterized by the steps of (a) connecting a plurality of reaction vessels each of which is provided with a stirrer to each other in a series arrangement such that when a liquid is continuously introduced into each reaction vessel the liquid overflows into the next reaction vessel, (b) continuously feeding a dispersion of zinc powder in an alkyl alcohol into only the first one of the plurality of reaction vessels to allow the dispersion in the first reaction vessel to overflow into the next reaction vessel and then into the remaining reaction vessels in turn while the stirrer of each reaction vessel is operated, (c) continuously feeding 1,1,2-trichloro-1,2,2-trifluoroethane into each of the reaction vessels while step (b) is performed thereby to form CTFE in each reaction vessel by continuous reaction of 1,1,2-trichloro-1,2,2-trifluoroethane with zinc powder to result in gradual conversion of zinc powder into zinc chloride, (d) continuously discharging CTFE from each reaction vessel while steps (b) and (c) are performed and collecting the discharged CTFE, and (e) continuously discharging a dispersion of the unreacted remainder of the zinc powder in a solution of zinc chloride in the alcohol from the last one of the plurality of reaction vessels while steps (b), (c) and (d) are performed.

In the above process usually it suffices to use two or three reaction vessels of the same effective volume.

By a process according to the present invention it is possible to easily and smoothly carry out a continuous reaction of R-113 with zinc powder dispersed in an alcohol such as methanol on an industrial scale. In this process the conversion of zinc powder into zinc chloride easily reaches 90% or above, and both zinc chloride and the alcohol can easily be recovered. Furthermore, the reaction in each reaction vessel remains in a steady state for a long period of time, so that CTFE and zinc chloride are formed at nearly constant rates, respectively, and therefore it is easy to perform incidental operations such as refining of CTFE and recovery of zinc chloride and alcohol.

BRIEF DESCRIPTION OF THE DRAWING

The single FIGURE is a diagrammatic illustration of an example of apparatus for a continuous process according to the invention.

DESCRIPTION OF THE PREFERRED EMBODIMENTS

As the starting compound this invention uses R-113 having a purity of 99.5% or above. That is, it suffices to use R-113 of the ordinary industrial grade.

The other reactant is a zinc powder which is desired to be at least 95 wt % in the content of metallic zinc and at least 99 wt % in the total content of zinc inclusive of zinc in the form of compounds. It is preferred to use zinc powder not larger than 100 μm in particle size. It is possible to use either a zinc powder which is prepared by the spray method and has needle-like particles or a zinc powder which is prepared by the distillation method and has spherical particles.

A lower alcohol is used as a liquid medium for the reaction. For example, the alcohol can be selected from methyl alcohol, ethyl alcohol and isopropyl alcohol, but it is preferred to use methyl alcohol in view of the cost and the efficiency of recovery. It suffices to use methanol of the ordinary industrial grade. It is preferable that the content of water in methanol or any other alternative alcohol is not more than 1000 ppm. If the content of water is higher the reaction between water and zinc chloride, which is formed by the principal reaction, to form a double salt becomes appreciable so that a considerable amount of solid matter precipitates in the reaction liquid, and hence it is likely that trouble arises about the flow of the reaction liquid through the piping connecting the reactors.

The single FIGURE in the drawing shows a case where a combination of three reaction vessels 10, 20, 30 is used in preparing CTFE by a continuous process according to the invention. Each of the three reaction vessels 10, 20, 30 is a stirred tank reactor.

Another stirred tank 40 is used for preparing and reserving a slurry of zinc powder in methanol. Efficient stirring is necessary for uniformly dispersing zinc powder in ethanol and constantly keeping a predetermined concentration of the slurry. The weight ratio of zinc powder to methanol is in the range from 1:1 to 1:4, and preferably in the range from 1:1.5 to 1:3.

Using a pump 42 the zinc powder slurry is continuously fed from the tank 40 into the first reactor 10 by an inlet at an upper section of the reactor 10. Since there is a great difference in specific gravity between zinc powder and methanol the zinc powder in the slurry settles if the slurry is stationary. Therefore, in designing the piping in the illustrated apparatus care should be taken to prevent stagnation of the slurry and to make appropriate selection of the types of pumps and valves.

R-113 is reserved in a tank 44, and a pump 16 is used to continuously feed R-113 into the first reactor 10 by an inlet at an upper section of the reactor.

The first reactor 10 is provided with a reflux tower 12 packed with Raschig rings, and an overflow pipe 14 extends from the first reactor 10 to an upper section of the second reactor 20. There is a pump 26 to continuously feed R-113 from the tank 44 into the second reactor 20 by an inlet at an upper section of the reactor. An overflow pipe extends from the second reactor 20 to an upper section of the third reactor 30, and there is a pump 36 to continuously feed R-113 from the tank 44 into the third reactor 30 by an inlet at an upper section of the reactor. Similarly to the first reactor 10, the second and third reactors 20 and 30 are provided with reflux towers 22 and 32, respectively. The three reflux towers 12, 22, 32 connect to a single pipe 46 which is provided with a pressure regulating valve 48 and extends to a refining station for refining CTFE. An overflow pipe 34 extends from the third reactor 30 to a recovery tank 50 which is provided with a discharge valve 52.

Each of the three reactors 10, 20, 30 is provided with a stirrer to carry out the reaction between R-113 and zinc powder while the zinc powder is well and uniformly dispersed in methanol. The type of the stirrer is not limited, but it is desirable to employ a stirrer having stirring blades of high efficiency such as, for example, anchor blades. It is suitable that the revolution speed of the stirrer is about 100 rpm or higher, though an optimum speed depends on various factors such as the shape of the reactor, concentration of the zinc powder slurry, shape of the stirring blades and the number of stirring blades.

Usually, at the start of the synthesis operation the reactors 10, 20 and 30 are each charged with a reaction liquid, which is a mixture of zinc powder, zinc chloride and methanol prepared by adding R-113 to a slurry of zinc powder in methanol. After regulating the temperature in each reactor the operation is started by continuously feeding R-113 and a zinc powder-methanol slurry to the first reactor 10. By reaction with R-113 zinc powder is gradually converted into zinc chloride while CTFE is formed by the reaction, and CTFE enters the reflux tower 12. Usually, in the first reactor 10 the molar ratio of $ZnCl_2$ to Zn becomes higher than 1:1, meaning that more than 50% of the initially supplied zinc powder reacts with R-113 within the first reactor.

As the reaction liquid (containing both Zn and $ZnCl_2$) in the reactor 10 continuously overflows, the reaction liquid is continuously fed into the second reactor 20 through the overflow pipe 14, while R-113 is continuously fed into the reactor 20 by the pump 26. In the reactor 20 too CTFE is formed while zinc is gradually converted into zinc chloride. In the second reactor 20 the molar ratio of $ZnCl_2$ to Zn becomes not lower than 3:1. By the overflow of the reaction liquid in the second reactor 20 the reaction liquid is continuously fed into the third reactor 30, while R-113 is continuously fed into the reactor 30 by the pump 36. In the reactor 30 still the reaction between zinc and R-113 takes place, and in this reactor 30 the molar ratio of $ZnCl_2$ to Zn becomes not lower than 9:1. The reaction liquid in the third reactor 30 overflows and flows into the recovery tank 50. Subsequently the collected reaction liquid is passed to a recovery station to recover methanol and zinc chloride separately.

The reaction in every reactor is carried out at a temperature in the range from about 70° C. to about 120° C. under a pressure in the range from 0 to about 8 kg/cm² (gauge pressure). The pressure in the reactors can be regulated by adjusting the pressure control valve 48 and the discharge valve 52. In general, the contents of trifluoroethylene and other low boiling point impurities in the obtained CTFE increase as the reaction temperature and reaction pressure become higher.

The crude CTFE discharged from the three reactors is collectively passed to a refining station to obtain CTFE of high purity by a conventional method. The purity of the crude CTFE formed by the above described continuous process is 90% or above, and the major impurities are R-113, 1,2-dichloro-1,1,2-trifluoroethane and trifluoroethylene.

As a by-product of the above described process zinc chloride having a purity of 97% or above is obtained. The impurities are only a double salt of zinc chloride with water and zinc oxide. Therefore, it is easy to obtain a solution of zinc chloride having a purity of 99.0% or above by treating the recovered zinc chloride with hydrochloric acid.

Assuming that the number of reactors used for the above described continuous process is m, and regarding the ratio of the concentration of zinc in the last (m'th) reactor in a steady state, $Z_m$ (mol/liter), to the concentration of zinc in the slurry continuously fed into the first reactor, $Z_0$ (mol/liter), the following equation (1) holds when the ultimate conversion of zinc (into zinc chloride) is not more than about 90% (i.e. $Z_m/Z_0 = 0.1$):

$$\frac{Z_m}{Z_0} = 1 - a\left(\frac{V_1}{F_1} \cdot \frac{V_2}{F_2} \cdot \frac{V_3}{F_3} \cdot \ldots \cdot \frac{V_m}{F_m}\right) \quad (1)$$

where $V_i$ ($i = 1, 2, \ldots m$) is the effective volume (liter) of each reactor (volume below the overflowing level), $F_i$ is the rate of feed of zinc slurry or reaction liquid (liter/hr) into each reactor, and $a$ (hr$^{-1}$) is a coefficient which is usually from 0.15 to 0.60 though it is somewhat variable depending on the reaction temperature and the value of $Z_0$.

In the equation (1), $V_i/F_i$ represents the residence time in each reactor. The reaction liquids in the respective reactors are different in specific gravity by 0.2 to 0.3, but by approximation it is possible to assume that: $F_1 = F_2 = \ldots = F_m = F$. The equation (1) indicates that the number of the reactor can be reduced if $V_i/F$ takes a large value and that the number of the reactors must be increased if $V_i/F$ takes a small value. Usually $V_i$ is made constant, and $V_i/F$ is adjusted to 1-5 hr to accomplish the continuous reaction by using two to four reactors of the same volume. In industrial practice it suffices to use two or three reactors.

The rate of feed of R-113 into each reactor is determined based on the feed rate of zinc to each reactor, and it is suitable that the feed rate of R-113 falls in the range from 0.90 $F \cdot Z_{i(0)}$ to 1.10 $F \cdot Z_{i(0)}$ mol/hr, where F is as described above, and $Z_{i(0)}$ is the concentration of zinc powder in the zinc slurry or reaction liquid introduced into each reactor ($i = 1, 2, \ldots m$).

The invention is further illustrated by the following nonlimitative examples.

EXAMPLE 1

The apparatus was generally as shown in the drawing, but the third reactor (30) was omitted.

Two identical pressure-proof tank reactors were used as the first and second reactors (10, 20). Each reactor had a nominal capacity of 70 liters, but the overflow port was positioned such that the effective volume of each reactor became 40.1 liters. Each reactor had a stirrer having anchor blades, and baffle plates were provided in the vicinity of the overflow port to prevent serious waving of the reaction liquid surface by stirring. The overflow pipe (14, 24) extending from each reactor was 25 mm in inner diameter. The reflux tower for each reactor was 40 mm in inner diameter and 900 mm in height and was packed with Raschig rings. The temperature in each reflux tower was maintained at 15°-20° C.

Preparatory to a continuous reaction operation using the above described apparatus, a first reaction liquid and a second reaction liquid were prepared each by dropwise adding R-113 to a mixture of 1 part by weight of zinc powder and 2 parts by weight of methanol. In both the first and second reaction liquids the molar ratio of total zinc to methanol, $(Zn + ZnCl_2)/CH_3OH$, was 1/4.1, but the two reaction liquids were different in the degree of conversion of zinc into zinc chloride. That is, $Zn/(Zn + ZnCl_2)$ was 39.6 mol % in the first reaction liquid and 12.0 mol % in the second reaction liquid.

At the start of the operation, the first reactor was charged with 40 liters of the above described first reaction liquid and the second reactor with 40 liters of the second reaction liquid. Then the temperature in each reactor was raised while the stirrer was operated, and a zinc slurry consisting of 1 part by weight of zinc powder and 2 parts by weight of methanol was continuously fed into the first reactor from the reservoir tank (40) at a constant rate of 12.0 kg/hr. In each reactor the stirrer was operated at a speed of 160 rpm, and by such stirring it was possible to maintain uniform dispersion of zinc powder in the liquid in each reactor. Simultaneously R-113 was continuously fed into each reactor, at a rate of 7.04 kg/hr into the first reactor and at a rate of 2.28 kg/hr into the second reactor. In the both reactors the reaction temperature was maintained at 90° C., and the pressure was 3 kg/cm$^2$ (gauge pressure). Under these conditions the continuous reaction was carried out for 7.5 hr.

In 7.5 hr, the yield of crude CTFE amounted to 43.06 kg (354.5 mol by measurement with a gas flowmeter). By analysis by gas chromatography, the crude CTFE contained 91.1% of CTFE, 5.6% of R-113, 3.1% of 1,2-dichloro-1,1,2-trifluroethane, 0.3% of trifluoroethylene and traces of other impurities.

The following Table shows the sequential results of the above described continuous reaction. The data in the table show that in about 2.5 hr from the start of the continuous reaction the composition of the reaction liquid in each reactor became nearly constant, that in each reactor the reaction liquid was uniform in composition, that a reaction liquid of nearly constant composition overflowed each reactor and that in each reactor crude CTFE was formed at a nearly constant rate. In the second reactor the conversion of zinc became more than 90 mol %. In this example the continuous reaction was terminated after the lapse of 7.5 hr, but it is possible to continue the same reaction for a far longer period of time since a steady state has already been established in each reactor.

In the Table, "outlet" of each reactor means sampling of the reaction liquid flowing in the overflow pipe extending from that reactor. The outflow of crude CTFE was measured with a gas flowmeter, and each of the indicated values incorporates temperature correction and excludes the amount of R-113 contained in the crude CTFE. The content of Zn in each reaction liquid was determined by filtering the reaction liquid with a filter paper, then drying the filter paper in vacuum and weighing the dried filter paper. The content of $ZnCl_2$ was found by titrating the filtrate with silver nitrate.

In this example, the residence time (V/F) in each reactor was about 3.5 hr, and the coefficient $a$ in the equation (1) was 0.162 by calculation.

|  | Reaction Time | | | | | | | | | | | | | |
|---|---|---|---|---|---|---|---|---|---|---|---|---|---|---|
|  | 0 | | 2.5 hr | | | | 5.0 hr | | | | 7.5 hr | | | |
|  | Reaction Vessel | | | | | | | | | | | | | |
|  | No. 1 | No. 2 | No. 1 | | No. 2 | | No. 1 | | No. 2 | | No. 1 | | No. 2 | |
|  | initial state | initial state | interior | outlet | interior | outlet | interior | outlet | interior | outlet | interior | outlet | interior | outlet |
| Zn/(Zn + ZnCl$_2$) (mol %) | 39.6 | 12.0 | 43.7 | 43.1 | 9.4 | 9.1 | 43.5 | 43.2 | 8.9 | 8.8 | 43.4 | 43.3 | 8.8 | 8.8 |
| (Zn + ZnCl$_2$)/CH$_3$OH (molar ratio) | 1/4.1 | 1/4.1 | 1/4.1 | 1/4.2 | 1/4.1 | 1/4.1 | 1/4.2 | 1/4.2 | 1/4.2 | 1/4.2 | 1/4.2 | 1/4.2 | 1/4.2 | 1/4.2 |
| Outflow of Crude CTFE (mol/hr) | 0 | 0 | 35.7 | | 11.6 | | 36.4 | | 11.3 | | 35.3 | | 11.5 | |

EXAMPLE 2

The apparatus used in Example 1 was modified by adding a third reactor (30) which was identical with the first and second reactors. The continuous reaction of Example 1 was repeated under the same operation conditions except that R-113 was continuously fed into the third reactor at a rate of 0.7 kg/hr.

As the result 36.03 kg of crude CTFE was obtained. The crude CTFE contained 90.9% of CTFE, 5.4% of R-113, 3.4% of 1,2-dichloro-1,1,2-trifluorothane, 0.3% of trifluoroethylene and traces of other impurities.

In the reaction liquid overflowing the third reactor the conversion of zinc into zinc chloride reached 96.5 mol %.

What is claimed is:

1. In a process of preparing chlorotrifluoroethylene by continuously reacting 1,1,2-trichloro-1,2,2-trifluoroethane with zinc powder dispersed in an alkyl alcohol,
   the improvement comprising the steps of:
   (a) connecting a plurality of reaction vessels each of which is provided with a stirrer to each other in a series arrangement such that when a liquid is continuously introduced into each reaction vessel the liquid overflows into the next reaction vessel;
   (b) continuously feeding a dispersion of zinc powder in an alkyl alcohol into only the first one of said plurality of reaction vessels to allow the dispersion in the first reaction vessel to overflow into the next reaction vessel and then into the remaining reaction vessels in turn while the stirrer of each reaction vessel is operated;
   (c) continuously feeding 1,1,2-trichloro-1,2,2-trifluoroethane into each of said plurality of reaction vessels while step (b) is performed thereby to form chlorotrifluoroethylene in each reaction vessel by continuous reaction of said 1,1,2-trichloro-1,2,2-trifluoroethane with said zinc powder to result in gradual conversion of said zinc powder into zinc chloride;
   (d) continuously discharging said chlorotrifluoroethylene from each reaction vessel while steps (b) and (c) are performed and collecting the discharged chlorotrifluoroethylene; and
   (e) continuously discharging a dispersion of the unreacted remainder of said zinc powder in a solution of said zinc chloride in said alcohol from the last one of said plurality of reaction vessels while steps (b), (c) and (d) are performed.

2. A process according to claim 1, wherein said alkyl alcohol is methyl alcohol.

3. A process according to claim 2, wherein the weight ratio of said zinc powder to methyl alcohol in said dispersion in step (b) is in the range from 1:1 to 1:4.

4. A process according to claim 3, wherein said weight ratio is in the range from 1:1.5 to 1:3.

5. A process according to claim 1, wherein said zinc powder in step (b) is not larger than 100 μm in particle size.

6. A process according to claim 1, wherein the reaction in each reaction vessel is carried out at a temperature in the range from 70° to 120° C. under a pressure in the range from 0 to 8 kg/cm$^2$ by gauge pressure.

7. A process according to claim 1, wherein the molar ratio of ZnCl$_2$ to Zn in the first reaction becomes not lower than 1:1.

8. A process according to claim 1, wherein the number of said plurality of reaction vessels is determined such that the molar ratio of ZnCl$_2$ to Zn in the last reaction vessel becomes not lower than 9/1.

9. A process according to claim 1, wherein the number of said plurality of reaction vessels is not more than three.

10. A process according to claim 9, wherein said plurality of reaction vessels have the same effective capacity.

11. A process according to claim 9, wherein the residence time in each reaction vessel represented by V (liter)/F (liter/hour) is in the range from 1 to 5 hours, wherein V is the effective capacity of each reaction vessel, and F is the rate of the feed of said dispersion in step (b) into the first reaction vessel.

* * * * *